US006455468B1

(12) United States Patent
Li et al.

(10) Patent No.: US 6,455,468 B1
(45) Date of Patent: Sep. 24, 2002

(54) SEED TREATMENT COMPOSITION

(75) Inventors: Paul Pen Hsiang Li, St. Paul; Ling-cheng Jian, Minneapolis, both of MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/560,117

(22) Filed: Apr. 28, 2000

(51) Int. Cl.$^7$ .............................................. A01N 59/00

(52) U.S. Cl. .................................................. 504/125

(58) Field of Search .......................... 424/600; 504/125

(56) References Cited

U.S. PATENT DOCUMENTS

| | | | |
|---|---|---|---|
| 4,488,901 A | 12/1984 | Farkas et al. | |
| 4,799,950 A | 1/1989 | Suzuki et al. | |
| 5,298,482 A | 3/1994 | Tanaka et al. | |
| 5,661,103 A | 8/1997 | Harms et al. | ................. 504/47 |
| 5,950,360 A | 9/1999 | Heinrich et al. | |

FOREIGN PATENT DOCUMENTS

| | | | |
|---|---|---|---|
| CA | 1 167 662 | | 5/1984 |
| CN | 1090970 A | | 8/1994 |
| CN | 1090970 | * | 8/1994 |
| CN | 1178207 | | 4/1998 |
| DE | 209340 | * | 4/1984 |
| DE | 255 871 | | 4/1988 |
| DE | 277 828 | | 4/1990 |
| DE | 277 831 | | 4/1990 |
| JP | 62-161701 | | 7/1987 |
| JP | 05209187 | | 8/1993 |
| RU | 1802977 | | 3/1993 |
| RU | 1819500 | | 6/1993 |
| SK | 278680 | | 12/1997 |
| SU | 709040 | | 1/1980 |
| SU | 1061718 | | 12/1983 |
| SU | 1493222 | | 7/1989 |
| SU | 965043 | | 1/1990 |
| SU | 1732901 | | 5/1992 |
| SU | 1757559 | | 8/1992 |
| SU | 1776361 | | 11/1992 |

OTHER PUBLICATIONS

The Agrochemicals Handbook, "chlormequat chloride," (Aug. 1987).
Alexander et al., "Effect of Pre–Sowing Seed Treatment by Potash on Drought Tolerance of Wheat under Rain–Fed Condition," *Potash Review*, Subject 9, pp. 1–3 (Jun., 1972).
Fauth et al., "Competence for Elicitation of $H_2O_2$ in Hypocotyls of Cucumber Is Induced by Breaching the Cuticle and Is Enhanced by Salicylic Acid," *Plant Physiol.*, 110:347–354 (1996).
Frias et al., "An Inoculation Method for Evaluating Resistance of Cacao to *Crinipellis perniciosa*," *Plant Disease*, 79(8):787–791 (1995).

Gazeau, "Increase of the freezing resistance (to—30° C.) of wheat seedlings (*Triticum aestivum* L.) with cryoprotective substances. Effects of these treatments on the ultrastructures of root meristematic cells," *Ann. Sci. Nat. Bot.*, 1:97–116 (1979) (with English language abstract). English Abstract Only.

Gazeau, "Accroissement de la résistance au froid (jusqu'à–30° C.) de plantules de Blé avec un milieu cryoprotecteur. Effets de ce traitement sur les ultrastructures de cellules parenchymateuses d'ébauches foliaires," *Can. J. Bot.*, 58:2520–2532 (1980) (with English language abstract). English Abstract Only.

Gazeau, "Accroissement de la résistance au froid de plantules de blé avec un milieu cryoprotecteur: variation de la température et de la durée du traitement d'imprégnation. Aspects physiologiques," *Can. J. Bot.*, 60:2857–2863 (1982) (with English Language Abstract). English Abstract Only.

Gazeau, "Influence de al température et de la durée d'un traitement cryoprotecteur sur la résistance au froid de plantules de blé. Étude ultrastructurale des nucléoles des ébauches foliaires," *Can. J. Bot.*, 63(4):663–671 (1985) (with English language abstract). English Abstract Only.

Guo et al., "Effects of Polyvinyl Alcohol Pretreatment on the Increase of Soybean Seed Vigour and its Protection Against Chilling Injury," *Acta Phytophysiologica Sinica*, 15(3):251–255 (1989) (with English language abstract). Eng. Abs only.

Jian et al., "The Studies of the Plant Cold–Resister and its Application in Rice Seedling Raising," Institute of Botany, Academia Sinica, Beijing China, 176–180 (undated).

Kushwaha et al., "Effect of Soil Moisture at Seeding, Nitrogen Levels and Pre–sowing Seed Treatments on Growth and Yield of Wheat Crop," *Mysore J. Agric. Sci.*, 22:318–326 (1988).

Li et al., "Studies on CCC increasing the drought resistance in peanut seedlings," *Acta Botanica Sinica*, 33(1):55–60 (1991) (with English language abstract). Eng Abs Only.

Li et al., "Effect of Calcium on the Cold–resistance of Rice Seedlings," *Acta Phytophysiologica Sinica*, 22(4):385–390 (1996) (with English language abstract). Eng Abs Only.

(List continued on next page.)

Primary Examiner—Alton Pryor
(74) Attorney, Agent, or Firm—Mueting, Raasch & Gebhardt, P.A.

(57) ABSTRACT

The present invention provides a chemical composition useful for treating seeds, including at least one choline-containing compound, a calcium-containing salt, a potassium-containing salt, and salicylic acid, and optionally containing an alkanolamine and/or glycerol. The present invention also provides methods of using the composition.

34 Claims, No Drawings

OTHER PUBLICATIONS

Mansour et al., "Salt acclimation of *Triticum aestivum* by choline chloride: Plant growth, mineral content, and cell permeability," *Plant Physiol. Biochem.*, 31(3):341–348 (1993).

Mozafar et al., "Salt tolerance of two differently drought–tolerant wheat genotypes during germination and early seedling growth," *Plant Soil*, 96:303–316 (1986).

Okey et al., "Salicylic Acid: A Factor In Systemic Resistance of Cacao to *Phytophthora Palmivora*," *Brighton Crop Prot. Conf. Pests Dis.*, 3:955–960 (1996).

Palva et al., "Salicylic Acid Induced Resistance to *Erwinia carotovora* subsp. *carotovora* in Tobacco," *Mol. Plant–Microbe Interact.*, 7(3):356–363 (1994).

Polegaev et al., "Using Chlorocholinechloride to Increase the Effectiveness of Cabbage Parent Plants," Abstract No. 10074064 *Izv. Timiryazev S–KH Akad.*, 0(2):103–112 (1992) (Abstract only).

Reggiani et al., "Effect of $K^+$ Ions on Polyamine Levels in Wheat Seedlings under Anoxia," *J. Plant Physiol.*, 142:94–98 (1993).

Seah et al., "The Effect of Salicylic Acid on Resistance in Wheat (*Triticum aestivum*) Seedling Roots against the Take–all Fungus, *Gaeumannomyces graminis* var. *tritici*," *Aust. J. Bot.*, 44(4):499–507 (1996).

Sen et al., "Correlation–coefficient between Yield and some Drought Tolerance capacity Measuring Parameters in 'Kalyan Sona' Wheat," *Food Farming Agriculture*, 14(1&2):1–2 (1981).

Siegrist et al., "Defense Responses in Infected and Elicited Cucumber (*Cucumis sativus* L.) Hypocotyl Segments Exhibiting Acquired Resistance," *Plant Phys.*, 105:1365–1374 (1994).

Thandapani et al., "Effect of Pre–sowing Seed Treatment with Chemicals and Growth Regulators for Drought Tolerance and Yield of Cotton (*Gossypium hirsutum* L) Under Rainfed Condition," *Madras Agricult. J.*, 73(12):668–675 (1986).

Wardle et al., "Stomatal Responses of *Phaseolus vulgaris* L. Seedlings to Potassium Chloride in the Nutrient Solution," *J. Exp. Bot.*, 30(119):1195–1200 (1979).

Yan et al., "Effects of Ultraviolet–B Radiation on Active Oxygen Metabolism and Membrane System of Rice Leaves," *Acta Phytophysiologica Sinica*, 22(4):379–384 (1996) (with English language abstract). Eng. Abs only.

* cited by examiner

SEED TREATMENT COMPOSITION

FIELD OF THE INVENTION

The present invention relates to chemical compositions useful for treating seeds. In particular, the present invention relates to a chemical composition useful for treating seeds to allow for planting and growing of seedlings under stressed conditions.

BACKGROUND OF THE INVENTION

Yield of various crops is affected by the conditions to which seeds and seedlings of such crops are exposed. Seeds are the part of a plant that typically contain an embryo, stored food, and a protective coat thereon. Young plants grown from seeds are generally referred to as seedlings. Such relatively small, immature forms are more susceptible to harsh environments and diseases than their mature counterparts.

Seeds and seedlings may be exposed to one of, or a combination of, cold, drought, salt, heat, pollutants, and disease, conditions that potentially retard or prevent the growth of crops therefrom. For example, temperature extremes are typical in the upper Midwest region of the United States. Furthermore, diseases evolved from pathogens and deterioration caused by fungi are potentially harmful to seeds and seedlings. Thus, it is desirable to treat seeds with compositions that render the seeds and seedlings grown therefrom more hardy when exposed to such conditions.

Various agents have been used to treat seeds to increase resistance of the plants to stressed conditions, such as cold, drought, salt, and fungi. Such agents include, for example, sodium methylphenyl-pentadienate, O,N-diaryl-carbamate derivatives, choline, salts of choline, chlorocholine chloride, hydroxy-benzimidazole derivatives, trichloroacetic acid, polyoxyalkylene-organo-siloxane block copolymer, 5-aminolevulinic acid, carboxy-propionyl-amino-pyrrolidine, ethanolamine, 2-trimethylammonio-ethanol chloride, salicylic acid, potassium chloride, and polyvinyl alcohol. Many such agents have been used in aqueous solutions to impregnate and/or coat seeds. They can be used alone, or in combination, but typically only show positive effects on limited types of plants. Thus, there is a need for seed treatment compositions that can be used on a wider variety of plants to improve their resistance to a variety of stress conditions.

SUMMARY OF THE INVENTION

The present invention provides a chemical composition useful for treating seeds. The composition includes choline chloride, a calcium-containing salt, a potassium-containing salt, and salicylic acid. The choline chloride can be present at a concentration of about 5 millimolar to about 25 millimolar. The calcium-containing salt can be selected from the group of calcium nitrate, calcium chloride, and combinations thereof. The calcium-containing salt can be present in the composition at a concentration of about 20 millimolar to about 30 millimolar. The potassium-containing salt can be selected from the group of potassium chloride, potassium nitrate, and combinations thereof. The potassium-containing salt can be present in the composition at a concentration of about 20 millimolar to about 25 millimolar. The salicylic acid can be present in the composition at a concentration of about 50 micromolar to about 100 micromolar.

Optionally, the composition includes glycerol, which can be present at a concentration of, for instance, about 0.5% by volume to about 3.0% by volume. Optionally, the composition includes chlorocholine chloride, which can be present at a concentration of, for instance, about 5 micromolar to about 4 millimolar of chlorocholine chloride. Optionally, the composition can include an alkanolamine, which can be present at a concentration of, for instance, about 15 millimolar to about 25 millimolar.

In another aspect of the present invention, the chemical composition is essentially choline chloride, a calcium-containing salt, a potassium-containing salt, salicylic acid, and glycerol, or the chemical composition is essentially choline chloride, chlorocholine chloride, a calcium-containing salt, a potassium-containing salt, salicylic acid, an alkanolamine, and glycerol.

The present invention also provides a chemical composition useful for treating seeds that includes chlorocholine chloride, a calcium-containing salt, a potassium-containing salt, salicylic acid, and an alkanolamine, and does not include ((4-chlorophenyl)methyl)-(1,1-dimethylethyl)-1,2,4-triazole-1-ethanol. The alkanolamine can be present in the composition at a concentration of about 15 millimolar to about 25 millimolar. The chlorocholine chloride can be present in the composition at a concentration of about 5 micromolar to about 4 millimolar. The calcium-containing salt can be selected from the group of calcium nitrate, calcium chloride, and combinations thereof. The calcium-containing salt can be present in the composition at a concentration of about 20 millimolar to about 30 millimolar. The potassium-containing salt can be selected from the group of potassium chloride, potassium nitrate, and combinations thereof. The potassium-containing salt can be present in the composition at a concentration of about 20 millimolar to about 25 millimolar. The salicylic acid can be present in the composition at a concentration of about 50 micromolar to about 100 micromolar. Optionally, the composition includes glycerol, which can be present at a concentration of, for instance, about 0.5% by volume to about 3.0% by volume.

Another aspect of the present invention provides a method for treating seeds with a composition of the present invention. The seed can be, for instance, a corn seed or a soybean seed. The method can also include planting the seed.

DETAILED DESCRIPTION OF PREFERRED EMBODIMENTS

The present invention provides seed treatment compositions useful for treating seeds of a variety of plants, including, for example, corn and soybean. A seed treatment composition according to the present invention can show desirable effects on plants when exposed to drought, cold, heat, and salt, for example.

For example, a seed treatment composition of the present invention can potentially enhance (i.e., increase) at least one of the following: seed emergence rate from soil, early vigor of seedlings; growth and development of seedlings; and crop yield. Significant improvements in root growth and development (e.g., one or more of branching, length of roots, diameter of roots, number of lateral roots, root nodules) have been observed in seedlings grown from seeds treated with a seed treatment composition of the present invention. Likewise, significant improvements in crop growth (e.g., one or more of increased height of the crop, increased plant fresh weight, minimized leaf chilling damage, minimized leaf drought damage) have been observed in crops grown from seeds treated with a seed treatment composition of the present invention. Although not intending to be limiting, it is believed that these positive effects result from stabilizing the cell membranes, in order to maintain cell properties as would exist under moderate environmental conditions.

The seed treatment compositions of the present invention include a combination of several components, typically at least four, preferably at least five, more preferably at least six, and most preferably at least seven components. It has been discovered that a mixture of the components described herein is effective on a wider variety of plants than are the individual components. Also, it has been discovered that a mixture of components described herein is typically more effective than are the individual components therein.

In some aspects of the invention, the compositions include choline chloride, a calcium-containing salt, a potassium-containing salt, and salicylic acid. Optionally, the compositions further include glycerol, chlorocholine chloride, or an alkanolamine. Alternatively, the compositions are essentially choline chloride, a calcium-containing salt, a potassium-containing salt, salicylic acid, and glycerol. In another aspect of the invention, the compositions include chlorocholine chloride, a calcium-containing salt, a potassium-containing salt, salicylic acid, and an alkanolamine, and do not include ((4-chlorophenyl)methyl)-(1,1-dimethylethyl)-1,2,4-triazole-1-ethanol. Optionally, the compositions further include glycerol. Alternatively, the compositions are essentially choline chloride, chlorocholine chloride, a calcium-containing salt, a potassium-containing salt, salicylic acid, an alkanolamine, and glycerol. Typically, the compositions of the present invention are used in combination with a diluent, such as water, to prepare an aqueous mixture.

Choline $((CH_3)_3N(OH)CH_2CH_2OH)$ is found in many plant species. It is a precursor of, for example, acetylcholine and lecithin. The inclusion of at least one choline-containing compound in the compositions of the present invention is thought to improve the effectiveness of enzymes present in cell membranes of plants. The choline-containing compound is typically used in the compositions of the present invention in the form of a salt. Preferred choline-containing compounds of the present invention include choline chloride $((CH_3)_3N(Cl)CH_2CH_2OH)$, chlorocholine chloride $((ClCH_2)_3N(Cl)CH_2CH_2OH)$, and combinations thereof. Preferred compositions include both choline chloride and chlorocholine chloride. Depending on the species of crops, type of seeds, and type of choline-containing compound utilized, a composition of the present invention can include different amounts of the choline-containing compound. Preferably, a composition includes about 5 micromolar to about 25 millimolar of the choline-containing compound. In general, more choline chloride is needed than chlorocholine chloride for a particular type of seed. Examples of preferred lower concentrations of choline chloride are about 20 millimolar for corn seeds and about 5 millimolar for soybean seeds. Examples of preferred high concentrations of choline chloride are about 25 millimolar for corn seeds and about 10 millimolar for soybean seeds. Examples of preferred lower concentrations of chlorocholine chloride are about 2 millimolar for corn seeds and about 5 micromolar for soybean seeds. Examples of preferred high concentrations of chlorocholine chloride are about 4 millimolar for corn seed, and about 10 micromolar for soybean seeds. It has been found, however, that if the concentration of chlorocholine chloride is too high, the composition may not be as effective, and can harm the seeds such that the seeds do not germinate.

Calcium (Ca) is a mineral nutrient. Minerals are needed for proper growth and function of cells. The calcium is provided in the form of a salt that is at least partially soluble in water. It is believed that the inclusion of at least one calcium-containing salt in the composition of the present invention enhances the ability of cells to interpret and react to external forces, such as harsh environmental conditions or disease. Preferred salts for use in the compositions of the present invention include calcium nitrate $(Ca(NO_3)_2)$, calcium chloride $(CaCl_2)$, and combinations thereof. Preferably, the calcium-containing salt is present in a composition of the present invention at a concentration of about 20 millimolar to about 30 millimolar.

Potassium (K) is also a mineral nutrient. The potassium is provided in the form of a salt that is at least partially soluble in water. The potassium salts are chosen such that they do not include a counterion that will precipitate the calcium out of solution. It is believed that the inclusion of at least one potassium-containing salt in the composition of the present invention enhances the ability of cells to react to external forces, such as harsh environmental conditions or disease. For example, potassium may play a role in controlling the osmotic potential in the cells of plants. Preferred salts according to the present invention include potassium chloride (KCl), potassium nitrate $(KNO_3)$, and combinations thereof. Preferably, the potassium-containing salt is present in a composition of the present invention at a concentration of about 20 millimolar to about 25 millimolar.

Salicylic acid $(HOC_6H_4COOH)$ is commonly utilized in the manufacture of aspirin (acetylsalicylic acid) or as a food preservative. Salicylic acid is included in the composition to enhance cell resistance to pathogens and other stresses. Preferably, salicylic acid is present in a composition of the present invention at a concentration of about 50 micromolar to about 100 micromolar.

Optionally, and preferably, the compositions of the present invention include glycerol. Glycerol $(C_3H_5(OH)_3)$ is commonly utilized as a food preservative. It is believed that glycerol is useful in the compositions of the present invention as a transporter of the other components of the compositions across cell membranes. Glycerol is preferably present in a composition of the present invention at a concentration of about 0.5% by volume to about 3.0% by volume. More preferably, glycerol is present at a concentration of about 1% by volume.

Optionally, the compositions of the present invention include an alkanolamine. The alkanolamine can be a compound of the formula: $HO-(CH_2)_n-NR^1R^2R^3$ or one of its acid addition salts, wherein n=2–5, and each of $R^1$ and $R^2$ are one of H or a $C_1-C_5$ alkyl, and $R^3$ is one of H, a $C_1-C_5$ alkyl, or a free electron pair. A preferred alkanolamine is 2-aminoethanol. It is a product of the decomposition of fatty acids within the cell membranes of plants. Depending on the crop and structure of the seed, a composition can include different amounts of an alkanolamine. Preferably, when treating corn seeds, for example, an alkanolamine is present in a composition at a concentration of about 15 millimolar to about 25 millimolar. Preferably the alkanolamine is 2-aminoethanol.

When treating seeds according to the present invention, seeds are contacted with the composition. Contacting seeds with the composition includes coating seeds or soaking seeds. Preferably, the seeds are contacted with the composition by coating. Seeds can be soaked in an aqueous solution containing a chemical composition of the invention. For example, corn seeds can be soaked for about 12 to about 24 hours. Some types of seeds (e.g., soybean seeds) may be sensitive to moisture. Thus, soaking such seeds for an extended period of time may not be desirable. Seeds can be coated using a mixture of the chemical composition and melted gelatin (available from Electro Microscopy Sciences, Fort Washington, Pa.) or other commercially available materials such as that available under the trade designation MAGNA-COAT from Gustafson Co., McKinney, Tex, can be used to coat such seeds. Alternatively, a mixture of the chemical composition and a paste derived from sticky rice can be used to coat seeds. Preferably, seeds coated using such a paste are planted very soon after coating. Such compositions are typically sprayed on the seeds, although other techniques can be used such as dip coating. Another method to coat seeds involves coating the inside wall of a round container with the composition, adding seeds, then rotating the container to cause the seeds to contact the wall and the composition (referred to herein as container coating"). Seeds can be coated by combinations of coating methods. While not intended to be limiting, the composition is still effective at least 75 days after coating.

The chemical composition of the present invention is particularly useful in treating corn seeds and soybean seeds. The following examples are included for aid in understanding the beneficial uses of the chemical composition. Variations to the following examples are encouraged and well within the scope of the present invention.

EXAMPLES

Example 1

Use of the Chemical Composition to Improve the Yield of Soybeans

Three varieties of soybean seeds: NK S19-90 (available from Northrup King Com., Stenton, Minn.), Evans (obtained from James Orf, Dept. of Agronomy and Plant Genetics, University of Minnesota, St. Paul), and Lambert (obtained from James Orf) were coated with the chemical composition. The composition was made by combining 1.8 grams $Ca(NO_3)_2$, 0.84 gram $KNO_3$, 0.005 gram salicylic acid, 0.12 gram choline chloride, 0.5 ml of glycerol, 0.3 ml of MAGNA-COAT gelatin and of 2.0 ml $H_2O$. Approximately one pound of seeds were coated with the composition using the container coating" method. Control seeds for each of the varieties were treated in 100% gelatin, no chemical composition.

The seeds were then planted after treatment in soil located in St. Paul, Minn. Four replications (i.e., plots) were used for each variety of seed, both control and coated. Each replication included 4 rows having a length of 12 feet with 85 seeds planted in each row.

Emergence rates for the seeds are given in Table 1. The NK S19-90 seeds appeared to have a better emergence rate for treated seeds as compared to the control seeds. The Evans and Lambert seeds did not show as significant an improvement in emergence rate.

TABLE 1

Emergence rates (%) of NK S19-90, Evans and Lambert Seeds.

| Date of examination (days after planting) | NK S19-90 | | Evans | | Lambert | |
|---|---|---|---|---|---|---|
| | Control | Treated | Control | Treated | Control | Treated |
| 11 days | 13 | 55 | 8 | 21 | — | — |
| 12 days | 73 | 81 | 60 | 50 | — | — |
| 15 days | 80 | 85 | 81 | 78 | 70 | 77 |

Plant growth and development of the treated and control seeds was also studied using plants 22 days from emergence and plants 58 days from emergence. The total plant weight was measured, including the weight of the roots. The number of root nodules was also counted.

The weights and number of root nodules of the 22-day-old plants are illustrated in Table 2. The results did not show any significant improvement when plants were grown from treated seeds versus control seeds. Visual observation of the NK S19-90 plants, however, appeared to indicate that plants grown from treated seeds were larger than plants grown from control seeds.

TABLE 2

Total fresh weight and number of root nodules of the 22-day old plants.

| | Total fresh weight (g/plant)[a] | | Number of nodules/plant[b] | |
|---|---|---|---|---|
| Variety | Control | Treated | Control | Treated |
| NK S19-90 | 7.3 | 7.0 | 24 | 31 |
| Evans | 6.2 | 5.2 | 16 | 29 |
| Lambert | 9.4 | 8.7 | — | — |

[a]Average of 10 plants, not significant at 5% level.
[b]Average of 10 plants, not significant at 5% level.

The weights, number of lateral roots, and number of nodules of the 58-day-old plants are illustrated in Table 3. The results did not show any significant improvement in total fresh weight when plants were grown from treated Evans and treated Lambert seeds as compared to their respective control seeds. Plants grown from treated NK S19-90 seeds, however, showed a 25% increase in total fresh weight on a per plant basis as compared to plants grown from control NK S19-90 seeds.

Likewise, the number of lateral roots was not significantly different in plants grown from treated Evans and treated Lambert seeds as compared to their respective control seeds. Plants grown from treated NK S19-90 seeds, however, showed an average of two more lateral roots on a per plant basis.

The number of root nodules was significantly greater in plants grown from treated Evans and treated Lambert seeds as compared to their respective control seeds. For example, on an average per plant basis, plants grown from treated Lambert seeds had 17 more root nodules than plants grown from control Lambert seeds. This improvement was not seen, however, in the NK S19-90 variety of seed.

TABLE 3

Plant Growth Performance at the age of 58 - day old from the emergence.

| | Total plant fresh weight (g/plant)[a] | | Number of lateral roots per plant[b] | | Number of nodules per plant[c] | |
|---|---|---|---|---|---|---|
| Plants | Control | Treated | Control | Treated | Control | Treated |
| A. Lambert | | | | | | |
| 1 | 99.9 | 228.6 | 11 | 15 | 9 | 36 |
| 2 | 226.6 | 197.0 | 8 | 14 | 13 | 28 |
| 3 | 181.6 | 232.8 | 7 | 12 | 12 | 38 |
| 4 | 160.0 | 102.7 | 12 | 9 | 22 | 29 |
| 5 | 92.0 | 132.7 | 13 | 10 | 18 | 30 |
| 6 | 187.5 | 103.6 | 11 | 10 | 10 | 28 |
| 7 | 223.5 | 133.2 | 9 | 10 | 5 | 20 |
| 8 | 111.2 | 155.0 | 11 | 10 | 18 | 15 |
| 9 | 102.3 | 111.0 | 7 | 14 | 7 | 45 |
| 10 | 72.2 | 224.6 | 5 | 15 | 6 | 20 |
| Average | 145.7 | 161.2 | 9.0 | 12.0 | 12.0 | 29.0 |

[a]not significant at 5% level.
[b]not significant at 5% level.
[c]significant at 5% level.

TABLE 3-continued

Plant Growth Performance at the age of 58 - day old from the emergence.

| Plants | Total plant fresh weight (g/plant)[a] | | Number of lateral roots per plant[b] | | Number of nodules per plant[c] | |
|---|---|---|---|---|---|---|
| | Control | Treated | Control | Treated | Control | Treated |
| B. Evans | | | | | | |
| 1 | 71.0 | 92.6 | 7 | 8 | 13 | 33 |
| 2 | 135.5 | 94.7 | 8 | 6 | 9 | 22 |
| 3 | 141.3 | 111.7 | 10 | 8 | 30 | 23 |
| 4 | 75.4 | 132.1 | 7 | 10 | 11 | 26 |
| 5 | 93.5 | 64.1 | 11 | 7 | 14 | 20 |
| 6 | 121.7 | 131.3 | 7 | 15 | 21 | 23 |
| 7 | 116.4 | 169.5 | 7 | 10 | 12 | 17 |
| 8 | 82.8 | 131.6 | 5 | 11 | 19 | 15 |
| 9 | 106.2 | 145.1 | 8 | 11 | 7 | 31 |
| 10 | 98.2 | 162.5 | 7 | 9 | 21 | 13 |
| Average | 104.2 | 123.5 | 8.0 | 11.0 | 16.0 | 22.0 |

[a]not significant at 5% level.
[b]not significant at 5% level.
[c]significant at 5% level.

| C. NK-S19-90 | | | | | | |
|---|---|---|---|---|---|---|
| 1 | 110.7 | 113.2 | 9 | 8 | 14 | 13 |
| 2 | 118.6 | 85.0 | 8 | 9 | 23 | 23 |
| 3 | 46.0 | 97.2 | 7 | 7 | 35 | 30 |
| 4 | 106.5 | 98.7 | 7 | 8 | 17 | 11 |
| 5 | 92.0 | 112.5 | 5 | 10 | 19 | 15 |
| 6 | 62.0 | 88.6 | 4 | 9 | 19 | 24 |
| 7 | 55.5 | 100.8 | 8 | 12 | 11 | 27 |
| 8 | 80.5 | 120.3 | 6 | 12 | 9 | 18 |
| 9 | 69.9 | 94.5 | 10 | 10 | 12 | 8 |
| 10 | 71.9 | 116.3 | 8 | 9 | 7 | 24 |
| Average | 81.4 | 100.7 | 7.0 | 9.0 | 17.0 | 19.0 |

[a]significant at 5% level.
[b]significant at 5% level.
[c]not significant at 5 % level.

Thus, treatment of Lambert seeds and treatment of Evans seeds did not result in a significant increase in either plant fresh weight or number of lateral roots. Treatment of Lambert seeds and treatment of Evans seeds did show a significant increase in the number of nodules. Treatment of NK-S19-90 seeds did result in a significant increase in plant fresh weight or number of lateral roots. Treatment of NK-S19-90 seeds did not show a significant increase in the number of nodules.

During this experiment there was a two-week period without rain in St. Paul, Minn. Thus, the field in which the seeds were planted was dry, imparting drought stress to the plants. Leaves of Lambert and Evans plants rapidly began to develop senescence (i.e., yellowing). This rate did not vary between plants grown from treated or control seeds. Leaves of NK S19-90 plants grown from treated seeds remained green, however.

Two rows of crops from each seed variety and treated/control combination were harvested from the center of each replication about 133 days after the seeds were planted. The crops were harvested from the center of each row in a length of 8 feet. Yield data for the crops is illustrated in Table 4. A 25% increase in yield (on a per 1,000 seed weight basis) resulted for the treated NK S19-90 seeds as compared to the control NK S19-90 seeds. An 8% increase in yield (on a per 1,000 seed weight basis) resulted from the treated Evans seeds as compared to the control Evans seeds. An improvement in yield was not observed, however, for the treated Lambert seeds.

TABLE 4

Effect of seed treatment on soybean yield.

| | | Seed Weight (grams) | | |
|---|---|---|---|---|
| Variety | Treatment | per row | per plant | per 1,000 seeds |
| NK | Control | 401.0 | 6.5 | 155.4 |
| S19-90[a] | Treated | 555.8 | 9.3 | 195.4 |
| Evans[b] | Control | 496.0 | 11.3 | 125.3 |
| | Treated | 584.0 | 13.5 | 135.5 |
| Lambert[c] | Control | 560.5 | 17.8 | 138.1 |
| | Treated | 622.8 | 20.5 | 139.6 |

[a]Significant at 1% level.
[b]Significant at 5% level.
[c]Not significant at 5% level.

Interestingly, the size of the seeds obtained from plants grown from treated NK S19-90 seeds was significantly larger than the size of the seeds obtained from plants grown from control NK S19-90 seeds. However, the protein and oil content of the three seed varieties was not different between control and treated seeds (data not shown).

An additional experiment was performed using the soybean variety Sturdy. Seeds were coated as described above, and four replications (i.e., plots) were used for both control and coated seeds. The seeds were planted in very sandy soil. The resulting crops were harvested and the grams per plot and bushels per acre measured (Table 5). There was a significant increase in yield.

TABLE 5

Soybean yield expressed by grams per plot or bushels per acre.

| Field | Treatment | Plot | grams/plot | bushels/acre |
|---|---|---|---|---|
| 1. | Control | 1 | 7832 | |
| | Control | 2 | 6379 | |
| | Control | 3 | 6674 | |
| | Control | 4 | 5947 | |
| | | | 6708 (Average) | 42.8 (Average) |
| | Treated | 1 | 9396 | |
| | Treated | 2 | 6810 | |
| | Treated | 3 | 7223 | |
| | Treated | 4 | 6901 | |
| | | | 7583 (Average) | 48.6 (Average) |
| 2.[a] | Control | | 1047 | 41.88 |
| | Control | | 1064 | 42.62 |
| | Control | | 1054 | 42.16 |
| | | | 1055 (Average) | 42.22 (Average) |
| | Treated | | 1480 | 59.18 |
| | Treated | | 1313 | 52.52 |
| | Treated | | 1154 | 46.16 |
| | Treated | | 1381 | 55.24 |
| | Treated | | 1237 | 49.48 |
| | Treated | | 1052 | 42.08 |
| | | | 1270 (Average) | 50.57 (Average) |

[a]A late maturing variety.

Example 2

Use of the Chemical Composition to Improve the Yield of Corn

Four varieties of corn seeds: N4242 (available from NK Company, Stenton, Minn.), Giza 2, SC-10 and SC-122 (obtained from Agricultural Research Center, Cairo, Egypt), were used. The composition was made by combining 4.724 grams/liter $Ca(NO_3)_2$, 2.525 grams/liter $K(NO)_3$, 0.016 gram/liter salicylic acid, 10 ml/liter glycerol, 2.50 grams/liter aminoethanol, 1.0 gram/liter choline chloride, 1.0 ml/liter chlorocholine chloride (National Bejing You-Low Chemical Manufacturing, Bejing, China, Cat. No. HG-818-75, Reg. No. PD86123-3), and 1.1 ml/liter $H_2SO_4$. The final pH of the composition was pH 6.7. About 3 kg of seeds were placed in a container and enough of the composition was added to cover the seeds. While soaking, the seeds were stirred occasionally. After about 20–24 hours of soaking, the composition was poured off and the seeds were allowed to air-dry. The seeds were then used for planting. Control seeds for each of the varieties were treated by soaking the seeds in water without the chemical composition, or by no soaking. Treated and control seeds were then planted within several days after treatment in soil. Those seeds grown in a growth chamber where exposed to a long day (greater than 14 hours of light).

Tables 6, 7, and 7 each contain data from three separate experiments conducted in three different years. Fresh weights of seedlings grown from treated and control seeds in a greenhouse are given in Table 6. Emergence rates of treated and control seeds and seedling fresh weight of the seedlings grown under cold temperatures from treated and control seeds in a growth chamber are given in Table 7. Seedling fresh weight and root fresh weight of seedlings grown from treated and control seeds in a greenhouse are given in Table 8. The treated seeds appeared to have better emergence rates as compared to the control seeds. The seedlings grown from treated seeds had a higher fresh weight and a higher root fresh weight as compared to the control seedlings.

TABLE 6

Corn seedling (N4242) fresh weight (F.Wt.) 20 days after emergence in the greenhouse.

| Treatment | Pots (5 plants per pot) | | | | Average F. Wt. per plant (g/plant) |
|---|---|---|---|---|---|
| | 1 | 2 | 3 | 4 | |
| | Total plant F. Wt. (g/5 plants) | | | | |
| Control* | 15.9 | 16.4 | 14.2 | 15 | 3.1 |
| Treated | 22.2 | 22.7 | 17.1 | 19.2 | 4.1** |

*Seeds were soaked with water
**24% increase in total F. Wt.

TABLE 7

Corn emergence rate and seedling growth (by fresh weight) of N4242 seeds 28 days after emergence, grown at 10° C. in a growth chamber.

| Treatment | Emergence Rate (%) | Seedling F. Wt. (g/plant) |
|---|---|---|
| Control 1* | 75 | 11.7 |
| Control 2** | 61 | 12.3 |
| Treated | 92 | 13.3*** |

*Seeds were soaked with water
**Seeds were not soaked with water
***Increase in plant fresh weight ranged from 8 to 13%

TABLE 8

Corn plant growth (by fresh weight) 21-days after emergence in the greenhouse.

| Corn variety | Treatment | Plant total fresh wt. (g/plant) | Root fresh wt. (g/plant) | % increase | |
|---|---|---|---|---|---|
| | | | | Plant | Root |
| Giza 2 | Treated | 85 | 14.7 | 70 | 126 |
| | Control | 50 | 6.5 | | |

TABLE 8-continued

Corn plant growth (by fresh weight) 21-days after emergence in the greenhouse.

| Corn variety | Treatment | Plant total fresh wt. (g/plant) | Root fresh wt. (g/plant) | % increase | |
|---|---|---|---|---|---|
| | | | | Plant | Root |
| SC-10 | Treated | 14.9 | 3.2 | 40 | 68 |
| | Control | 10.2 | 1.9 | | |
| SC-122 | Treated | 15.0 | 3.6 | 38 | 58 |
| | Control | 10.7 | 2.3 | | |

Treated and control seeds were planted in soil in three separate locations in Minnesota. Table 9 shows the resulting number of lateral roots and yield of seedlings grown from treated and control seeds. Seedlings grown from treated seeds showed an increase in the number of lateral roots and increased yield.

TABLE 9

Corn root development and yield in seedlings grown in the field at St. Paul, Waseca, and Lamberton locations.

| Location | No. of lateral roots* per plant | | Yield** (Lbs/10 ears) | | % increase in yield |
|---|---|---|---|---|---|
| | Control | CM6 | Control | CM6 | |
| St. Paul | 55 | 71 | 3.2 | 4 | 25 |
| Waseca | 36 | 43 | 2.8 | 3.2 | 14 |
| Lamberton | 39 | 43 | 2.6 | 3.5 | 35 |

*Roots from 3 randomly collected plants
**Yield from 10 randomly collected ears

Treated and control seeds were planted in St. Paul, Minn. Table 10 shows seedlings grown from treated seeds did not exhibit an increase in the number of ears. However, the total seed weight per 15 plants grown from treated seeds and the average seed weight of seeds obtained from plants grown from treated seeds was higher as compared to those from control seeds.

TABLE 10

Yield comparison for plants grown in St. Paul, Minnesota.

| Treatment | No. plot | No. plants | No. ears | Total seed wt. of 15 plants (grams) | Average seed wt. (g/plant) | % increase in seed weight |
|---|---|---|---|---|---|---|
| Control | 1. | 15 | 23 | 2171 | 144.7 | |
| | 2. | 15 | 26 | 2308 | 153.8 | |
| | 3. | 14 | 24 | 2232 | 159.4 | |
| | 4. | 15 | 22 | 2361 | 157.4 | |
| | | | Ave.: | 2268* | 153.8* | |
| Treated | 1. | 15 | 25 | 2740 | 183.0 | 26 |
| | 2. | 15 | 23 | 3027 | 201.8 | 31 |
| | 3. | 14 | 26 | 3180 | 227.0 | 42 |
| | 4. | 15 | 24 | 2722 | 181.4 | 15 |
| | | | Ave.: | 2918* | 198.3* | 28 |

*Significant at 5% level.

An additional experiment was performed by coating corn seeds of the variety N4242. The composition was made by combining 1.8 grams $Ca(NO_3)_2$, 0.8 grams $K(NO)_3$, 5 milligrams salicylic acid, 1 ml aminoethanol, 0.5 ml chlorocholine chloride (National Bejing You-Low Chemical Manufacturing, Bejing, China, Cat. No. HG-818-75, Reg.

No. PD86123-3), 1.0 ml glycerol, 0.3 ml MAGNA-COAT, and 2 ml water.

Seeds were prepared by coated as described above, and four replications (i.e., plots) were used for both control and coated seeds. The seeds were planted in very sandy soil. The resulting crops were harvested and the gram weight per 40 ears and gram weight per 1000 seed measured (Table 11). There was a significant increase in yield.

TABLE 11

Yield of corn raised from CM6-coated seeds.

| Treatment | Plot | Gram weight per 40 ears | Gram weight per 1000 seed |
|---|---|---|---|
| Control | 1 | 4495 | 245 |
| Control | 2 | 4154 | 240 |
| Control | 3 | 4131 | 240 |
| Control | 4 | 4449 | 243 |
|  |  | 4307 (Average) | 242 (Average) |
| Treated | 1 | 5516 | 254 |
| Treated | 2 | 5788 | 259 |
| Treated | 3 | 4790 | 247 |
| Treated | 4 | 5403 | 258 |
|  |  | 5374 (Average) | 255 (Average) |

All patents, patent applications, and publications disclosed herein are incorporated by reference in their entirety, as if individually incorporated. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A chemical composition useful for treating seeds, comprising:
    choline chloride;
    a calcium-containing salt;
    a potassium-containing salt; and
    salicylic acid.

2. The chemical composition of claim 1 further comprising glycerol.

3. The chemical composition of claim 2 wherein the glycerol is present in the composition at a concentration of about 0.5% by volume to about 3.0% by volume.

4. The chemical composition of claim 1 further comprising chlorocholine chloride.

5. The chemical composition of claim 4 further comprising an alkanolamine.

6. The chemical composition of claim 5 wherein the alkanolamine is present in the composition at a concentration of about 15 millimolar to about 25 millimolar.

7. The chemical composition of claim 1 wherein the choline chloride is present in the composition at a concentration of about 5 millimolar to about 25 millimolar.

8. The chemical composition of claim 4 wherein the chlorocholine chloride is present in the composition at a concentration of about 5 micromolar to about 4 millimolar.

9. The chemical composition of claim 1 wherein the calcium-containing salt is selected from the group of calcium nitrate, calcium chloride, and combinations thereof.

10. The chemical composition of claim 1 wherein the calcium-containing salt is present in the composition at a concentration of about 20 millimolar to about 30 millimolar.

11. The chemical composition of claim 1 wherein the potassium-containing salt is selected from the group of potassium chloride, potassium nitrate, and combinations thereof.

12. The chemical composition of claim 1 wherein the potassium-containing salt is present in the composition at a concentration of about 20 millimolar to about 25 millimolar.

13. The chemical composition of claim 1 wherein the salicylic acid is present in the composition at a concentration of about 50 micromolar to about 100 micromolar.

14. A method for treating seeds comprising contacting a seed with a composition comprising:
    choline chloride;
    a calcium-containing salt;
    a potassium-containing salt; and
    salicylic acid.

15. The method of claim 14 wherein the composition further comprises glycerol.

16. The method of claim 14 wherein the composition further comprises chlorocholine chloride.

17. The method of claim 16 wherein the composition further comprises an alkanolamine.

18. The method of claim 14 wherein the seed is selected from the group of a corn seed and a soybean seed.

19. The method of claim 14 further comprising planting the seed.

20. A chemical composition useful for treating seeds, the composition consisting essentially of:
    choline chloride;
    a calcium-containing salt;
    a potassium-containing salt;
    salicylic acid; and
    glycerol.

21. A chemical composition useful for treating seeds, the composition consisting essentially of:
    choline chloride;
    chlorocholine chloride;
    a calcium-containing salt;
    a potassium-containing salt;
    salicylic acid;
    an alkanolamine; and
    glycerol.

22. A chemical composition useful for treating seeds comprising:
    chlorocholine chloride;
    a calcium-containing salt;
    a potassium-containing salt;
    salicylic acid; and
    an alkanolamine;
    wherein the composition does not include ((4-chlorophenyl)methyl)-(1,1-dimethylethyl)-1,2,4-triazole-1-ethanol.

23. The composition of claim 22 wherein the composition further comprises glycerol.

24. The chemical composition of claim 23 wherein the glycerol is present in the composition at a concentration of about 0.5% by volume to about 3.0% by volume.

25. The chemical composition of claim 22 wherein the alkanolamine is present in the composition at a concentration of about 15 millimolar to about 25 millimolar.

26. The chemical composition of claim 22 wherein the chlorocholine chloride is present in the composition at a concentration of about 5 micromolar to about 4 millimolar.

27. The chemical composition of claim 22 wherein the calcium-containing salt is selected from the group of calcium nitrate, calcium chloride, and combinations thereof.

28. The chemical composition of claim 22 wherein the calcium-containing salt is present in the composition at a concentration of about 20 millimolar to about 30 millimolar.

29. The chemical composition of claim 22 wherein the potassium-containing salt is selected from the group of potassium chloride, potassium nitrate, and combinations thereof.

30. The chemical composition of claim 22 wherein the potassium-containing salt is present in the composition at a concentration of about 20 millimolar to about 25 millimolar.

31. The chemical composition of claim 22 wherein the salicylic acid is present in the composition at a concentration of about 50 micromolar to about 100 micromolar.

32. A method for treating seeds comprising contacting a seed with a composition comprising:

chlorocholine chloride;

a calcium-containing salt;

a potassium-containing salt;

salicylic acid; and an alkanolamine;

wherein the composition does not include ((4-chlorophenyl)methyl)-(1,1-dimethylethyl)-1,2,4-triazole-1-ethanol.

33. The method of claim 32 wherein the composition further comprises glycerol.

34. The method of claim 32 further comprising planting the seed.

* * * * *